US00PP27100P3

(12) United States Plant Patent

Klemm et al.

(10) Patent No.: US PP27,100 P3

(45) Date of Patent: Aug. 23, 2016

(54) *CALIBRACHOA* PLANT NAMED 'KLECA14263'

(50) Latin Name: ***Calibrachoa* sp.**
Varietal Denomination: KLECA14263

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 109 days.

(21) Appl. No.: 14/544,271

(22) Filed: Dec. 15, 2014

(65) Prior Publication Data

US 2016/0174448 P1 Jun. 16, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Anne Grunberg
(74) *Attorney, Agent, or Firm* — James M. Weatherly; Bethany R. Roahrig; Cochran Freund & Young, LLC

(57) ABSTRACT

A new *Calibrachoa* plant particularly distinguished by having pink flowers with a red-purple eye and a semi-upright form and plant habit, is disclosed.

1 Drawing Sheet

Genus and species: *Calibrachoa* sp.
Variety denomination: 'KLECA14263'.

BACKGROUND OF THE NEW PLANT

The present invention comprises a new and distinct variety of *Calibrachoa*, botanically known as *Calibrachoa* sp., and hereinafter referred to by the variety name 'KLECA14263'. 'KLECA14263' originated from a controlled-cross between the female *Calibrachoa* variety 'KLECA10216' (U.S. Plant Pat. No. 22,893) and the proprietary male *Calibrachoa* variety 'J 904' (unpatented).

In May 2010, two *Calibrachoa* parental lines, the female variety 'KLECA10216' and the male *Calibrachoa* variety 'J 904' were crossed via a controlled cross in Stuttgart, Germany and seeds were obtained. The seeds were sown and plants were grown for evaluation. A plant line was selected in May 2011, having pink flowers with a red-purple eye and subsequently named 'KLECA14263'. In May 2011, 'KLECA14263' was first vegetatively propagated by vegetative tip cuttings in Stuttgart, Germany. 'KLECA14263' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Pink flowers with a red-purple eye; and
2. A semi-upright form and plant habit.

DESCRIPTION OF THE PHOTOGRAPH

This new *Calibrachoa* plant is illustrated by the accompanying photograph which shows flowers grown in a pot. The photograph is of a four-month-old plant grown outdoors in Stuttgart, Germany in July 2014.

The colors shown are as true as can be reasonably obtained by conventional photographic procedures.

DESCRIPTION OF THE NEW VARIETY

The following detailed descriptions set forth the distinctive characteristics of 'KLECA14263'. The data which define these characteristics were collected from asexual reproductions carried out in Stuttgart, Germany. Data was collected on eleven-week-old plants grown in Stuttgart, Germany in May 2014. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.
- *Parentage*.—Female: The female *Calibrachoa* 'KLECA10216' (U.S. Plant Pat. No. 22,893). Male: Proprietary male *Calibrachoa* 'J 904' (unpatented).

Plant description:
- *Life cycle*.—Annual.
- *Form*.—Semi-upright.
- *Habit*.—Semi-upright.
- *Height (from soil line to top of foliage)*.—5.0 cm.
- *Spread*.—23.0 cm.

Propagation: Vegetatively propagated.
- *Type cuttings*.—Tip cuttings.
- *Time to produce a rooted cutting*.—3 weeks.

Stems:
- *Stem color*.—RHS 138B.
- *Pubescence*.—Absent.
- *Stem description*.—Stem diameter: 0.1 cm (stem diameter including side shoots: 6.0 cm). Stem length: 11.0 cm. From soil line to first node: 1.5 cm. Total length: 12.0 cm. Internode length: 1.6 cm.

Leaves:
*Arrangement*.—Alternate, simple, sessile.
*Shape*.—Elliptic.
*Apex*.—Obtuse to slightly acute.
*Base*.—Attenuate.
*Margin*.—Entire.
*Surface*.—Smooth.
*Surface pubescence*.—Absent.
*Venation*.—Pinnate.
*Venation color*.—Upper surface: RHS 144A. Lower surface: RHS 145A.
*Length*.—2.5 cm.
*Width*.—0.7 cm.
*Color*.—Upper surface: RHS N138A. Lower surface: RHS 138B.
*Fragrance*.—Absent.
Flowers: Single flowers.
*Flowering habit*.—Flower attitude erect, single, axillary.
*Flower type*.—Determinate inflorescence.
*Flowering requirements*.—A minimum of light sun is required.
*Duration of flowers*.—7 days.
*Corolla*.—Smooth texture.
*Shape*.—Trumpet shaped.
*Fragrance*.—Absent.
Flower buds:
*Surface*.—Smooth.
*Length*.—1.5 cm.
*Diameter*.—0.6 cm.
*Shape*.—Iregular to oblong.
*Color*.—RHS N11B and RHS 59A.
Peduncle:
*Length*.—2.2 cm.
*Diameter*.—0.1 cm.
*Color*.—RHS 144C.
*Texture*.—Smooth.
*Anthocyanin color*.—RHS N77A.
Flower description:
*Flower depth*.—3.0 cm.
*Flower tube length*.—1.8 cm.
*Flower tube diameter*.—0.7 cm.
*Flower diameter*.—3.4 cm.
*Pedicel color*.—RHS 144C.
*Calyx*.—Funnel-shaped.
Sepals:
*Shape*.—Lanceolate.
*Apex*.—Acute.
*Margin*.—Entire.
*Length*.—1.4 cm.
*Diameter*.—0.2 cm.
*Sepal color*.—Upper and lower surfaces: RHS 143A.
Petals:
*Shape*.—Heart-shaped.
*Length*.—1.2 cm.
*Apex*.—Obverse.
*Margin*.—Entire, weak undulation.
*Base*.—Open and fused in the tube.
*Pubescence*.—Absent.
*Lobe length*.—0.9 cm.
*Lobe width*.—1.5 cm.
*Color*.—Lobe color: Upper surface: RHS 75C. Lower surface: RHS 75D. Corolla tube color: Inner: RHS 71A. Outer: RHS 177D.
*Fragrance*.—Absent.
Reproductive organs:
*Stamen number*.—5.
*Stamen color*.—Anther color: RHS 21A. Filament color: RHS 1B. Pollen color: RHS 21A.
*Ovary*.—Placenta arrangement: Ovate. Pistil number: 1. Pistil length: 0.1 cm. Stigma color: RHS 144B. Style length: 1.1 cm. Style color: RHS 144D.
Fruit/seed set: Little.
Disease/insect resistance: None observed.

COMPARISON WITH PARENTAL LINES AND KNOWN VARIETY

'KLECA14263' is distinguished from its parents as described in Table 1:

TABLE 1

Comparison with Parental Lines

| Trait | Variety 'KLECA14263' | Female parent 'KLECA10216' | Male Parent 'J 904' |
|---|---|---|---|
| Flower color | RHS 75C and RHS 71A | RHS 75C and RHS 61B | RHS 69C and RHS 55A |

'KLECA14263' is most similar to the commercial *Calibrachoa* plant named 'KLECA10216' (the female parent), U.S. Plant Pat. No. 22,893, commercially known as MiniFamous Light Pink+Eye. Differences between the two varieties are described in Table 2:

TABLE 2

Comparison with Similar Variety

| Trait | Variety 'KLECA14263' | Calibrachoa 'KLECA10216' |
|---|---|---|
| Flower color | RHS 75C and RHS 71A | RHS 75C and RHS 61B |
| Growing habit | More compact, tight than 'KLECA10216' | More vigorous than 'KLECA14263' |

We claim:

1. A new and distinct variety of *Calibrachoa* plant named 'KLECA14263' as illustrated and described herein.

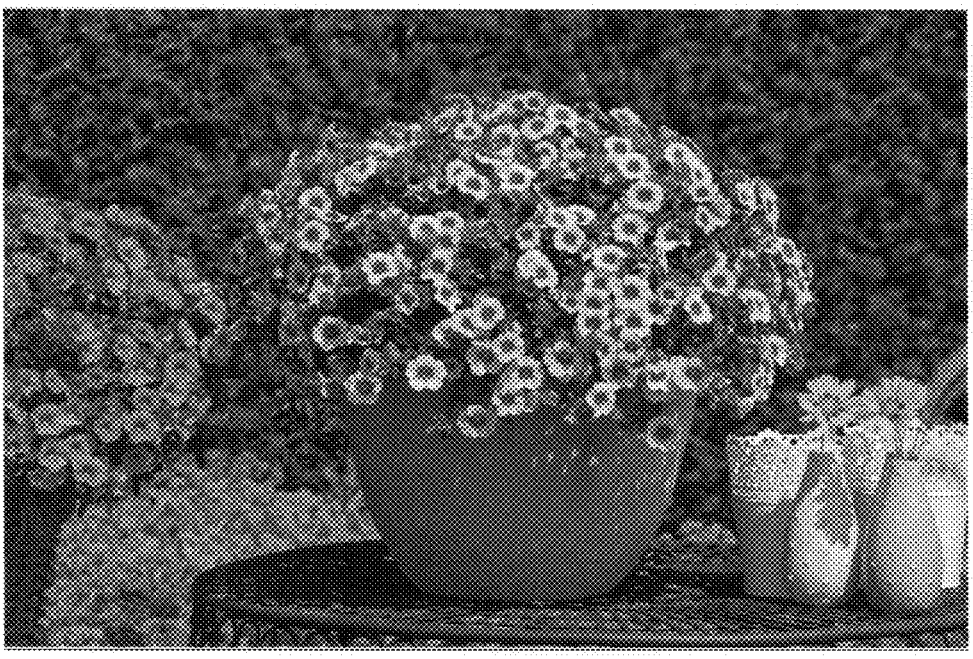

* * * * *